(12) United States Patent
Hillman

(10) Patent No.: US 6,964,760 B2
(45) Date of Patent: Nov. 15, 2005

(54) ANTIMICROBIAL POLYPEPTIDE, NUCLEIC ACID, AND METHODS OF USE

(75) Inventor: Jeffrey Daniel Hillman, Gainesville, FL (US)

(73) Assignee: University of Florida Research Foundation, Gainvesville, FL (US)

( * ) Notice: Subject to any disclaimer, the term of this patent is extended or adjusted under 35 U.S.C. 154(b) by 540 days.

(21) Appl. No.: 10/013,036

(22) Filed: Oct. 30, 2001

(65) Prior Publication Data

US 2002/0128186 A1 Sep. 12, 2002

Related U.S. Application Data

(60) Continuation-in-part of application No. 09/361,900, filed on Jul. 27, 1999, now Pat. No. 6,391,285, which is a division of application No. 08/871,924, filed on Jun. 10, 1997, now Pat. No. 5,932,469.

(51) Int. Cl.[7] .......................... A61K 7/28; A61K 38/16; C07K 14/315
(52) U.S. Cl. ............................. 424/49; 424/50; 514/13; 530/326
(58) Field of Search ........................ 424/49, 50; 514/2, 514/12, 13; 530/326

(56) References Cited

U.S. PATENT DOCUMENTS

| | | | |
|---|---|---|---|
| 5,352,450 A | | 10/1994 | Koga et al. |
| 5,650,320 A | | 7/1997 | Caufield et al. |
| 6,218,362 B1 | * | 4/2001 | Lavoie et al. .................. 514/13 |
| 6,391,285 B1 | * | 5/2002 | Hillman ....................... 424/50 |

FOREIGN PATENT DOCUMENTS

| | | |
|---|---|---|
| EP | 0 543 195 A2 | 10/1992 |
| WO | WO 96/40865 | 12/1996 |
| WO | WO 98/17685 | 4/1998 |

OTHER PUBLICATIONS

Rudinger. In *Peptide Hormones*, J. A. Parsons, ed. University Park Press, Baltimore, pp. 1–7, 1976.*
European Search Report for European Patent Application 98928967.3–2106–US9812003.

EMBL database entry AAP91366.

Gutierrez, et al., "Insertional Mutagenesis and Recovery of Interrupted Genes of Streptococcus mutans by Using Transposon Tn917: Preliminary Characterization of Mutants Displaying Acid Sensitivity and Nutritional Requirements" *Journal of Bacteriology*, vol. 178, No. 14, pp. 4166–4175, Jul. 1997.

Mota–Meira et al., "Purification and Structure of Mutacin B–Ny266: A New Lantibiotic Produced by Streptococcus Mutans", *FEBS Letters*, 410, pp. 275–279, Feb. 1997.

Hillman, et al., "Genetic and Biochemical Analysis of Mutacin 1140, A Lantibiotic from Streptococcus Mutans", *Infection and Immunity*, vol. 66, No. 6, pp. 2743–2749, Nov. 1997.

Smith, et al., "Probing Structural Heterogeneity in Mutacin 1140, a Novel Lantibiotic". Fortieth International Experimental Nuclear Magnetic Resonance Conference, Orlando, Florida, Feb. 28–Mar. 5, P034–73 (1999).

Smith, et al., "Covalent and Initial Three–Dimensional Structure of the Lantibiotic Mutacin 1140", Southeast Magnetic Resonance Conference, Tallahassee, Florida P45–102, Fall (1999).

Mota–Meira, et al., "MICs of Mutacin B–Ny266, Nisin A, Vancomycin, and Oxacillin against Bacterial Pathogens", *Antimicrobial Agents and Chemotherapy*, pp. 24–29, Jan. 2000.

Smith, et al., "Covalent Structure of Mutacin 1140 and a Novel Method for the Rapid Identification of Lantibiotics", *Eur. J. Biochem.*, 267, pp. 6810–6816, 2000.

* cited by examiner

*Primary Examiner*—Lorraine Spector
*Assistant Examiner*—Stephen Gucker
(74) *Attorney, Agent, or Firm*—Lisa M. W. Hilllman; McDonnell Boehnen Hulbert & Berghoff LLP

(57) ABSTRACT

Antimicrobial compounds and compositions and uses thereof, including the treatment and prevention of bacterial infections are described. The compounds and compositions include lantibiotic polypeptides and the nucleic acid sequences encoding the polypeptides. The compounds and compositions are useful as antimicrobials in antibiotic pharmaceutical preparation and as an antimicrobial or antiseptic dentifrice.

19 Claims, 1 Drawing Sheet

ANTIMICROBIAL POLYPEPTIDE, NUCLEIC ACID, AND METHODS OF USE

PRIORITY

This application is a continuation-in-part of U.S. Ser. No. 09/361,900, filed Jul. 27, 1999, now U.S. Pat. No. 6,391,285 B1, which is a divisional of U.S. Ser. No. 08/871,924, filed Jun. 10, 1997, now U.S. Pat. No. 5,932,469. This application and patent are incorporated herein, in their entirety.

GOVERNMENT RIGHTS

The invention was made with government support under a research project supported by National Institute of Dental Research Grant No. DE04529. The government has certain rights in this invention.

TECHNICAL FIELD OF THE INVENTION

This invention relates to novel lantibiotics and methods of their use.

BACKGROUND OF THE INVENTION

The phenotypically similar bacteria collectively known as the mutans streptococci are considered major etiologic agents responsible for dental caries. The species most commonly associated with human disease is *Streptococcus mutans*. Pathogenicity of *S. mutans* includes the ability to produce antimicrobial substances generally referred to as bacteriocin-like inhibitory substances (BLIS) or bacteriocins. Bacteriocins produced by *S. mutans* are known as mutacins. These substances are produced by microorganisms to provide a selective force necessary for sustained colonization in a milieu of densely packed competing organisms found in dental plaque.

To date, most bacteriocins remain only partially characterized because they are made in small quantities and only under special cultivation conditions. In addition, mutacins are known to be difficult to isolate from liquid medium. The spectrum of activity and chemical and physical properties of mutacins can vary widely.

Certain bacteriocin peptides or mutacins produced by *S. mutans* have recently been characterized as belonging to a group of peptides called lantibiotics (Novak, et al. (1996) Anal. Biochem. 236:358–360). Lantibiotics are polycyclic peptides that typically have several thioether bridges, and which can include the amino acids lanthionine or β-methyllanthionine. In addition, lantibiotics can contain α,β-unsaturated amino acids such as 2,3-didehydroalanine and 2,3-didehydro-2-aminobutyric acid, which are the products of post-translational modification of serine and threonine residues, respectively.

Certain lantibiotics have demonstrated antibiotic activity, mainly against Gram-positive bacteria (Bierbaum and Sahl (1993) Int. J. Med. Microbiol. Virol. Parasitol. Infect. Dis. 278:1–22). Nisin and epidermin are the best known examples of the 20 or so lantibiotics which have been identified to date. They are ribosomally synthesized as prepropeptides that undergo several post-translational modification events, including dehydration of specific hydroxyl amino acids and formation of thioether amino acids via addition of neighboring cysteines to didehydro-amino acids. Further post-translational processing involves cleavage of a leader sequence, which can be coincident with transport of the mature molecule to the extracellular space. A mature lantibiotic molecule is usually about 20 to 35 residues having thioether linkages that result in cyclical segments and provide a substantial degree of rigidity to the rodlike structure.

Current evidence indicates that the biological activity of certain lantibiotics, e.g., those known as "type A" lantibiotics, depends on the association of a number of molecules with the membrane of a target bacterium to form ion channels, thereby resulting in desynergization. Rapid loss of all biosynthetic processes occurs, resulting in death of the target cell. Other lantibiotics known as "type B" lantibiotics, can exert their effect by specifically inhibiting certain enzymes.

The genetics of lantibiotic production have been studied in several species of bacteria. In general, it has been found that a structural gene for a preprolantibiotic is clustered with genes that encode products responsible for post-translational modifications of the lantibiotic. In certain instances, these genes are known to form an operon or operon-like structure (see e.g., Schnell, et al. (1992) Eur. J. Biochem. 204:57–68). Production of lantibiotics can also require accessory proteins, including processing proteases, translocators of the ATP-binding cassette transporter family, regulatory proteins, and dedicated producer self-protection mechanisms. For example, at least seven genes have been shown to be involved in epidermin biosynthesis.

Lantibiotic properties have been exploited in certain products that are commercially available. The lantibiotic nisin has been developed as a food preservative that has been given "Generally Recognized as Safe (GRAS)" status by the federal Food and Drug Administration (FDA). It is employed as a food preservative in more than 40 countries and is used in preference to nitrites and nitrates. The oral toxicity of this compound, and presumably other lantibiotics, is very low in rats ($LD_{50}$=7 g/kg; Hurst, (1981) Adv. Appl. Microbiol. 27:85–123). Other applications for nisin, including its use as a mouth rinse (Howell et al, (1993) J. Clin. Periodontal 20:335–339), are actively being examined by a large number of laboratories.

The discovery of new lantibiotic compounds having antibiotic activity can be particularly important in view of the increased resistance to presently available antibiotics in certain pathogenic microorganisms. Novel lantibiotic compounds having unique or superior activity against particularly virulent pathogenic bacteria are desirable in providing new weapons in the arsenal against bacterial infection.

BRIEF SUMMARY OF THE INVENTION

It is an object of the invention to provide a novel lantibiotic. It is another object of the invention to provide methods of controlling bacterial growth or multiplication with a lantibiotic.

One embodiment of the invention provides an isolated lantibiotic comprising SEQ ID NO: 6 or a biologically functional variant thereof.

Another embodiment of the invention provides an isolated pre-lantibiotic comprising SEQ ID NO: 12 or a biologically functional variant thereof.

Still another embodiment of the invention provides a method of controlling the growth of bacteria in an animal comprising administering to the animal a composition comprising a lantibiotic shown in SEQ ID NO: 6, or a biologically functional variant thereof, whereby growth is controlled.

Yet another embodiment of the invention provides a method of treating or ameliorating a bacterial infection in an animal comprising administering to the animal a composition comprising a lantibiotic shown in SEQ ID NO: 6, or a biologically functional variant thereof. The infection is treated or ameliorated.

Even another embodiment of the invention provides a method for controlling bacterial growth or multiplication in or on an object. The method comprises applying a lantibiotic shown in SEQ ID NO: 6, or a biologically functional variant thereof, to the object, whereby bacterial growth or multiplication is controlled.

The subject invention therefore concerns novel lantibiotic polypeptides and polynucleotides encoding those polypeptides. The polypeptides are related to bacteriocins, e.g. mutacins, produced by microbes for providing a selective advantage for the microbe. The invention includes methods of use which exploit the advantageous activities or properties of the polypeptides or polynucleotides.

BRIEF DESCRIPTION OF THE FIGURES

FIG. 1A shows traditional selective (ethanethiol) chemical modification, mass spectrometry, and Edman sequencing. FIG. 1B shows double labeling/Edman sequencing and selective labeling/mass spectrometry. FIG. 1C shows NMR spectrometry (which is in perfect agreement with all the other data). Question marks indicate uncertainty about the type of post-translational modification. Filled circles at the C terminus indicate lack of Edman sequencing data. Vertical lines (1B) indicate involvement in thioether bridge formation. Dha, 2,3-didehydroalanine; Dhb, 2,3-didehydrobutyrine; Abu$_S$, S-2-aminobutyric acid.

DETAILED DESCRIPTION OF THE INVENTION

Figure 1:
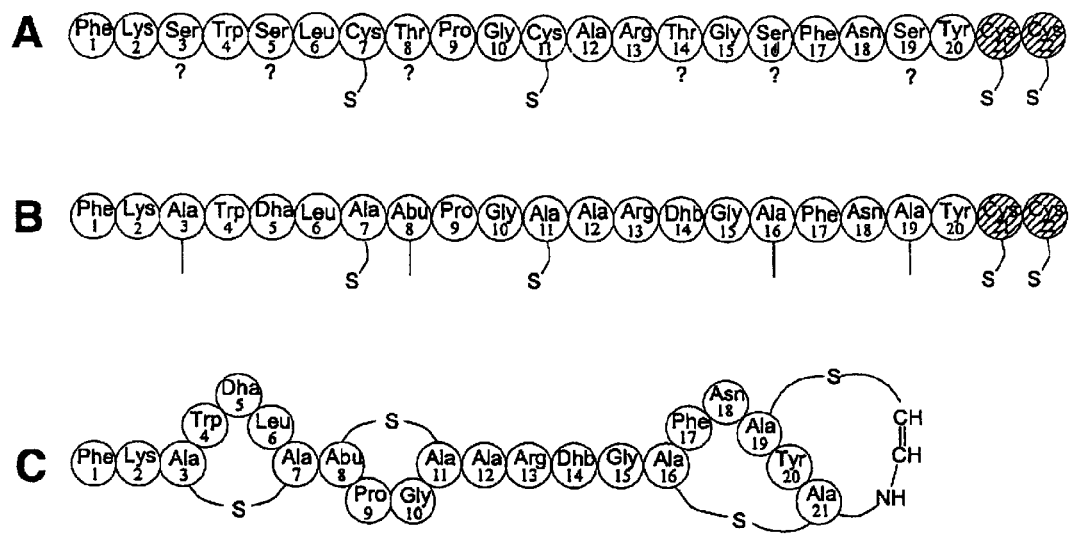
FIGS. 1A-C shows the structure of mutacin 1140 derived from different sets of experients.

Described herein is a novel lantibiotic and biologically functional variants thereof, first identified from a strain of *S. mutans* designated JH1140. A lantibiotic of the invention, here termed mutacin 1140, like other lantibiotics, is a polycyclic peptide that is the product of post-translational modification of a precursor protein translated from a single gene transcript in a host organism. The structure of mutacin 1140 is shown in SEQ ID NO: 6 and is shown below:

One of the evolutionary strategies utilized by microorganisms for enhanced competitiveness with competing strains is the synthesis of antibiotic agents to which competitive strains are sensitive. A wild-type strain of *S. mutans*, called JH1000 is the parent of an ethyl methane sulfonate-induced mutant called JH1005 and spontaneous mutant, known as JH1140. Both JH1005 and JH1140 have good colonization properties and produce a potent broad spectrum lantibiotic. As described below, lantibiotics of the invention inhibit the growth of representative strains of a wide variety of bacterial species. In addition, virtually all known *S. mutans* strains tested are sensitive to lantibiotics of the invention.

Analysis of isogenic mutants of these strains demonstrated good correlation between lantibiotic production and colonization potential in both a rodent model and human subjects. Utilizing genetic methods, the transcript responsible for lantibiotic activity has been identified and sequenced. SEQ ID NO:1 shows a polynucleotide encoding a polypeptide responsible for lantibiotic activity. The corresponding gene is termed lanA. SEQ ID NO:2 shows a deduced amino acid sequence of the transcript produced by an open reading frame present in SEQ ID NO:1. SEQ ID NO:2 is a pre-proprotein form of a lantibiotic which, after proteolytic cleavage and processing by other factors present in the host organism, results in the synthesis of mutacin 1140 (SEQ ID NO:6).

The proper synthesis of mutacin 1140 in a host microorganism requires the presence of other enzymes to process the precursor form of the protein into the effective and active form of the peptide lantibiotic. A polynucleotide encoding one of those enzymes, here designated lanB, has also been cloned and sequenced and is presented as SEQ ID NO:3. SEQ ID NO:4 shows the deduced amino acid sequence of the open reading frame contained in SEQ ID NO:3. Qi et al. has also reported a sequence for lanB (Appl. Eviron. Microbiol. 66:3221–3229 (2000)).

Initially, the chemical structure presented in SEQ ID NO:5, was believed to be the correct structure of mutacin 1140. However, it is was recognized that there could be

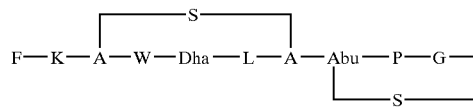 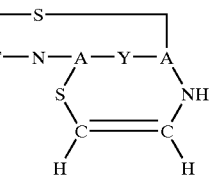

Lactate-dehydrogenase deficient mutants of *S. mutans* have been studied for their potential use in replacement therapy for dental caries. Without the trait of LDH, fermentation of carbohydrates by *S. mutans* employs alternate pathways for pyruvate metabolism that yields significant amounts of neutral end products. Therefore, LDH deficient strains exude less total acids into the environment. As a result, LDH deficient mutants of *S. mutans* are less cariogenic than other strains of *S. mutans*. Thus, LDH deficient *S. mutans* strains are being studied as effector strains for replacement therapy for dental caries. However, in order to be an effective replacement strain, *S. mutans* must demonstrate superior competitive colonization properties to compete against other strains of the species and to prevent subsequent recolonization by wild-type strains. Accordingly, effort has been conducted to find strains that have both superior colonization properties as well as an LDH-deficiency phenotype.

some minor differences between the structure of SEQ ID NO:5, and the actual structure of the molecule, due to limitations in the analytical techniques used to elucidate the structure of the molecule. It was then determined that the actual structure of mutacin 1140 is the structure shown in SEQ ID NO:6.

As used herein, the term "mutacin 1140" is intended to apply to polypeptide lantibiotics produced by *S. mutans* strain 1140, as well as biologically functional variants produced by other Streptococcus strains. Therefore, the term mutacin 1140 includes, for example, allelic variants that are produced by other strains of *S. mutans* or other closely related strains of other species.

The invention includes biologically functional variants of a lantibiotic shown in SEQ ID NO:6 that have substantial biological activity. That is, about 90% to about 110% of the biological activity of a lantibiotic polypeptide comprising SEQ ID NO:6. Such variants can include amino acid substitutions selected according to general rules known in the art so as have little effect on activity.

Guidance concerning how to make phenotypically silent amino acid substitutions is provided in Bowie et al., *Science*, 247:1306–1310 (1990). This reference describes two main strategies for studying the tolerance of an amino acid molecule to change.

The first strategy exploits the tolerance of amino acid substitutions by natural selection during the process of evolution. By comparing amino acid sequences in different species, the amino acid positions that have been conserved between species or strains can be identified. These conserved amino acids are likely important for protein function. In contrast, the amino acid positions in which substitutions have been tolerated by natural selection indicate positions that are not critical for protein function. Thus, positions tolerating amino acid substitution can be modified while still maintaining biological activity of a lantibiotic.

The second strategy uses genetic engineering to introduce amino acid changes at specific positions of a cloned gene to identify regions critical for protein function. For example, site-directed mutagenesis or alanine-scanning mutagenesis (the introduction of single alanine mutations at every residue in the molecule) can be used (Cunningham et al., *Science*, 244:1081–1085 (1989)). The resulting variant molecules can then be tested for biological activity by, for example, bioassay of lantibiotic activity, see Example 2.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved. Reference herein to conservative amino acid substitution is intended to mean the interchangeability of amino acid residues having similar side chains or size. For example, tolerated conservative amino acid substitutions involve replacement of amino acids within the following groups: group 1: ala, pro, gly, glu, asp, gln, asn, ser, thr; group 2: cys, ser, tyr, thr; group 3 val, ile, leu, met, ala, phe; group 4: lys, arg, his; and group 5: phe, tyr, trp, his. Additionally, Dha can be substituted for alanine. An amino acid substitution can also be non-conservative. Non-conservative amino acid substitutions replace an amino acid with an amino acid of a different group. A lantibiotic peptide of the invention can comprise any combination of conservative or non-conservative amino acid substitutions.

In one embodiment of the invention, a conservative amino acid substitution can occur at amino acid number 13 of SEQ ID NO:6, and comprises a Lys in place of an Arg (SEQ ID NO:7). A conservative substitution can also occur at amino acid number 19 of SEQ ID NO:6 and comprises a Dha in place of an Ala (SEQ ID NO:8). A conservative substitution can also occur, for example at amino acid number 6 of SEQ ID NO:6 and comprises a Phe in place of a Leu (SEQ ID NO:9). A lantibiotic of the invention can comprise any combination of one, two, or three of these substitutions.

For example a lantibiotic peptide of the invention can comprise a substitution at amino acid number 6 of SEQ ID NO:6, which comprises a Phe in place of a Leu, a substitution at amino acid number 13, which comprises a Lys in place of an Arg, and a substitution at amino acid number 19, which comprises a Dha in place of an Ala (SEQ ID NO:10). Another example comprises a substitution at amino acid number 6 of SEQ ID NO:6, which comprises a Phe in place of a Leu, and a substitution at amino acid number 13, which comprises a Lys in place of an Arg (SEQ ID NO:11).

In one embodiment of the invention, a lantibiotic comprises 1, 2, 3, or 4 substitutions. In another embodiment of the invention, a lantibiotic comprises 5, 6, 7, or more substitutions. In one embodiment of the invention conservative amino acid substitutions occur at amino acid positions 1, 2, 4, 5, 6, 13, 19, or combinations thereof (based on SEQ ID NO:6). In another embodiment of the invention amino acid substitutions occur at positions 1, 2, 4, 5, 6, 9, 10, 12, 13, 14, 15, 17, 18, 19, 20, or combinations thereof (based on SEQ ID NO:6). In another embodiment of the invention conservative amino acid substitutions or non-conservative amino acid substitutions occur at amino acid positions 1, 2, 4, 5, 6, 13, 19, or combinations thereof. Insertions or deletions can also occur at amino acid positions 1, 2, 4, 5, 6, 13, 19, or combinations thereof.

In another embodiment of the invention, lantibiotic molecules can comprise amino acid deletions, insertions, inversions, and repeats such that the molecules have substantial biological activity. A lantibiotic can comprise 1, 2, 3, 4, 5, 6, 7, or more amino acid deletions, insertions, inversions, or repeats.

Another embodiment of the invention comprises a pre-lantibiotic of SEQ ID NO:12 and variants thereof. A pre-lantibiotic is a form of a lantibiotic peptide that does not have thioether bridges formed. Variants include conservative amino acid substitutions at positions 1, 2, 4, 5, 6, 13, 19 or combinations thereof.

Lantibiotic molecules of the present invention also include fusion of a lantibiotic polypeptide with another compound, such as a compound to increase the stability and/or solubility of the polypeptide (e.g., polyethylene glycol) and fusion of a polypeptide with additional amino acids, such as an IgG Fc fusion region peptide, a leader or secretory sequence, or a sequence facilitating purification.

Lantibiotics of the present invention can be isolated from culture medium in which its native host organism, i.e., a Streptococcal organism, has been grown. Two Streptococcal strains that produce a lantibiotic of the invention have been deposited with the American Type Culture Collection, Rockville, Md., as Accession Numbers 55676 (JH1140) and 55677 (JH 1000). In addition, other coding sequences important in post-translation modification can be cloned and transformed into a Streptococcal species or strains of other bacterial species such that a recombinant lantibiotic is produced. See, e.g., Qi et al., Appl. Eviron. Microbiol. 66:3221–3229 (2000).

A potential complexity in the introduction of the phenotype for mutacin 1140 into a new strain is the fact that the peptide undergoes post-translational modifications by other genetic elements in the host strain, including, for example, lanB, lanC and lanD. See, e.g., Qi et al. These genetic elements should be present in a host strain or should be transferred to a host strain along with a polynucleotide encoding a lantibiotic of the invention in order to provide proper post-translational modification of a recombinant lantibiotic. Post-translational modification genes are contained within the genome of strain JH1140. Mutagenesis studies on JH1140 can identify all necessary components for post-translational modification. In another embodiment of the invention, lantibiotics can be synthesized ex vivo. A number of techniques exist for the synthesis of polypeptide molecules by relatively conventional organic chemical techniques. For example, solid phase polypeptide synthesis permits the creation of polypeptides the size of lantibiotics of the invention such that they can readily be synthesized outside of a microbial host.

A lantibiotic of the invention can be used as an antibiotic. Since a lantibiotic is produced by a common Streptococcal strain present in human mouths, it is expected to be relatively non-toxic to human species and other animals. This conclusion is further buttressed by its analogous characteristic to existing antibiotics, such as epidermin, which are known to be quite non-toxic to mammals. Lantibiotics of the invention can be applied to an area in which it is desired to inhibit microbial growth. For example, a lantibiotic of the invention can be used in a dentifrice. A dentifrice is a composition used for cleansing teeth. A dentifrice can also comprise, for example, abrasives, detergents, binders, medicaments, caries preventatives, excipients, carriers, and flavoring agents. A dentifrice can be a liquid, paste or powder.

In one embodiment of the invention a lantibiotic is bacteriostatic, that is, it inhibits the growth or multiplication of bacteria. In another embodiment of the invention a lantibiotic is bacteriocidal, that is, it kills bacteria. A lantibiotic can have bacteriostatic action, bacteriocidal action, or both activities against a given bacterium.

Lantibiotics of the invention can be used to control bacterial growth. "Control bacterial growth" means to reduce bacterial growth, to reduce bacterial multiplication, to kill bacteria, or combinations thereof. For example, a lantibiotic can be applied to an area in which it is desired to control bacterial growth. An area can be, for example, animal tissue, such as human tissue, food, plants, or an inanimate object. Where a lantibiotic of the invention is used to control the growth of bacteria in an animal, a pharmaceutical composition comprising a lantibiotic of the invention is administered to the animal. The growth of the bacteria is controlled. The animal can be any type of mammal or non-mammal. In one embodiment of the invention, the animal is a human.

In one embodiment of the invention a lantibiotic is used to treat or ameliorate a bacterial infection in an animal. The lantibiotic is administered to the animal and the infection is treated or ameliorated.

A therapeutically effective dose or effective amount of a lantibiotic of the invention refers to that amount of lantibiotic that controls bacterial growth in a desired location.

A therapeutically effective dose or effective amount can be estimated initially either in bioassays or in animal models, such as mice, rabbits, dogs, or pigs. An animal model can also be used to determine the appropriate concentration range and route of administration. Such information can then be used to determine useful doses and routes for administration in, for example, humans. Therapeutic efficacy and toxicity can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. In one embodiment of the invention, pharmaceutical compositions exhibit large therapeutic indices. The data obtained from bioassays and animal studies is used in formulating a range of dosage for animal use. The dosage contained in such compositions can be within a range of circulating concentrations that include the $ED_{50}$ with little or no toxicity. The dosage varies within this range depending upon the dosage form employed, sensitivity of the patient, and the route of administration.

An exact therapeutically effective dosage will be determined by a practitioner of skill in the art, in light of factors related to the animal that requires treatment. Dosage and administration are adjusted to provide sufficient levels of a lantibiotic or to maintain the desired effect. Factors that can be taken into account include the severity of the bacterial infection, general health of the subject, age, weight, and gender of the subject, diet, time and frequency of administration, drug combination(s), reaction sensitivities, and tolerance/response to therapy.

An effective amount of lantibiotic to be applied to an inanimate object or to food can be determined by one of skill in the art using routine experimentation.

Compositions of the invention can comprise a pharmaceutically acceptable carrier. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art.

Compositions of the invention can also contain excipients, such as water, saline, glycerol, sucrose, alcohols, invert sugar, glucose, polyols fats, waxes, semisolid and liquid polyols, natural or hardened oils, lactose, corn starch, talc, stearic acid, mixed polymers of glycolic acid and lactic acid dextrose, malodextrin, ethanol, or the like, singly or in combination. Compositions of the invention can also comprise substances such as wetting agents, emulsifying agents, or pH buffering agents. Liposomes can also be used as a carrier for a composition of the invention, see e.g., N. Weiner, Drug Develop. Ind. Pharm. 15:1523 (1989); "Liposome Dermatics" (Springer Verlag 1992) and Hayashi, Gene Therapy 3:878(1996). Further details on techniques for formulation and administration can be found in the latest edition of Remington's Pharmaceutical Sciences (Maack Publishing Co., Easton, Pa.).

Pharmaceutical compositions of the invention can be administered by any number of routes including, but not limited to, oral, mucosal, intravenous, intramuscular, intradermal, intra-arterial, intramedullary, intrathecal, intraventricular, transdermal, subcutaneous, intraperitoneal, intranasal, enteral, topical, sublingual, or rectal means.

Pharmaceutical compositions for oral administration can include, for example, tablets, pills, dragees, capsules, liquids, gels, syrups, slurries, suspensions, and the like, for ingestion by the patient. Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can include substances that increase the viscosity of the suspension, such as sodium carboxymethyl cellulose, sorbitol, or dextran. Additionally, suspensions of a lantibiotic of the invention can be prepared as oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers can also be used for delivery. Optionally, the suspension can also contain suitable stabilizers or agents that increase the solubility of the compounds to allow for the preparation of highly concentrated solutions.

For topical or nasal administration, penetrants appropriate to the particular barrier to be permeated are used in the formulation. Such penetrants are generally known in the art.

A lantibiotic of the invention can be active against Gram positive or Gram negative bacterial species such as *Acinetobacter* sp., *Actinobacillus* sp., *Actinomyces* sp. such as *A. israelii, A. naeslundii, A. viscosus, Bacillus* sp. such as *Bacillus anthracis, Brucella* sp., *Bordetella* sp., *Campylobacter* sp., *Clostridium* sp., *Corynebacterium* sp. such as *C. diphtheriae, Enterococcus* sp., *Enterobacter* sp., *Haemophilus* sp., *Legionella* sp., *Listeria* sp. such as *L. monocytegenes, Lactobacillus* sp. such as *L. salivarius, Micrococcus* sp., *Mycobacterium* sp. such as *M. phlei, Neisseria* sp., *Pseudomonas* sp., *Propionobacterium* sp. such as *P. acnes, Staphylococcus* sp. such as *S. aureus, Streptococcus* sp. such as *S. mutans, S. mitis, S. pyogenes, Vibrio* sp., and *Flavobacterium* sp. Lantibiotics of the invention are also active against the *Enterobacteriaceae*, for example, *Buttiauxella, Cedecea, Citrobacter, Edwardsiella, Enterobacter, Escherichia, Ewingella, Hafnia, Klebsiella, Kluyvera, Koserella, Leminorella, Moellerella, Morganella, Obesumbacterium, Proteus, Providencia, Rhanella, Salmonella, Shigella, Serratia, Tatumella, Yersinia, Xenorhabdus.*

Gram negative species of bacteria are sensitive to lantibiotics of the invention. However, a higher concentration of a lantibiotic can be required. For example, 2-, 5-, or 10-fold higher concentrations of the lantibiotic can be required for Gram negative bacteria than for Gram positive bacteria. The addition of a membrane-disrupting agent, such as EDTA or other membrane-disrupting agent can increase the efficacy of a lantibiotic of the invention. It should be understood that the examples and embodiments described herein are for illustrative purposes only and that various modifications or changes in light thereof will be suggested to persons skilled in the art and are to be included within the spirit and purview of this application and the scope of the appended claims. All references cited this disclosure are incorporated by reference in their entirety.

EXAMPLE 1
Purification of a Lantibiotic

A lantibiotic was purified from *Streptococcus mutans* JH1140 using the following procedure:

Four liter batches of Todd-Hewitt broth (THB; Difco) containing 0.5% LE agarose (SeaKem) were sterilized and poured into 90 mm petri plates. The plates were dried overnight at 37° C. A pure culture of JH1140 on a brain-heart infusion starter plate was used to inoculate 3 ml of THB and the cell suspension was vortexed for 10 sec. About 0.3 ml of the cell suspension was spread on the surface of a BHI agar plate and incubated overnight at 37° C. in a candle jar.

A 10-pronged inoculator was ethanol-flame sterilized and used to inoculate JH1140 from the spread plate into evenly spaced stabs in the plates prepared as described above. The plates were incubated in candle jars at 37° C. for 72 hours. The agar was entirely scraped from the plates and placed into centrifuge bottles. The bottles were stored overnight at −20° C.

The bottles were then centrifuged at room temperature for 60 min. at 4,000 rpm in a Sorvall RC2B centrifuge and then for an additional 30 min. at 8,000 rpm. The supernatant was recovered and passed through Whatman #1 filter paper in a Buchner funnel.

To the filtered extract (ca. 3,000 ml) in a 4 L beaker, 100 ml of chloroform was added. The solution was placed on a magnetic stirrer and agitated at high speed for 120 min. The stir bar was removed and the solution was allowed to stand overnight undisturbed.

The aqueous (upper) phase was aspirated off and discarded. The chloroform layer, containing a milky white flocculent, was divided into 50 ml conical centrifuge tubes and centrifuged at ca. 4,000 rpm for 8 min. Residual aqueous material was removed by aspiration. The clear chloroform layer was removed using a Pasteur pipette, leaving the flocculent, which was washed 2 times with 5 ml of chloroform. Chloroform was evaporated from the flocculent using a stream of nitrogen gas; the tube was placed in a 45–50° C. water bath during this process to promote evaporation.

The dried residue was dissolved in 0.5 ml of 50% ethanol; undissolved material was removed by centrifugation at 13,000×g for 2 min. at room temperature. The clarified fraction including the lantibiotic was then stored at −20° C. until further use. The lantibiotic was further purified to homogeneity using HPLC (C18 column) and 5 to 60% acetonitrile gradient.

EXAMPLE 2
Bioassay of Lantibiotic Activity

Antimicrobial activity of the lantibiotic was determined by the following procedure: 5 ml of Todd Hewitt broth (THB) were inoculated with *S. rattus* strain BHT-2 (resistant to 1 mg/ml streptomycin); and grown overnight standing at 37° C. 0.02 ml of fractions to be tested for lantibiotic activity were serially 2-fold diluted in distilled water in microtiter wells. Top agar was prepared containing BHI broth, 0.75% agar, 1 mg/ml streptomycin, and 1:10,000 diluted overnight *S. rattus* BHT-2 culture from above at 42° C.; 0.2 ml was pipetted into each microtiter well. After 5 min. at room temperature to allow agar to set, the plate was incubated at 37° C. overnight.

The minimal inhibitory concentration (MIC) was determined as the reciprocal of the highest dilution of the test fraction which inhibited growth of *S. rattus* BHT-2 by visual inspection.

EXAMPLE 3
Spectrum of activity of the Lantibiotic

Single colonies of a strain producing mutacin 1140 were stab inoculated into brain THB and incubated overnight in candle jars at 37° C. Three drops of an overnight THB culture of the indicator strain were mixed with 3 ml of molten top agar and poured evenly over the surface of the plate. After an additional 24 hours of incubation, clear zones surrounding the test strain were measured.

Representative strains of various bacteria were tested for their sensitivity to the inhibitory activity of the mutacin 1140 produced by a JH1140 strain by using a overlay technique. In addition to *S. mutans*, most Gram positive organisms were found to be sensitive, including *Streptococcus mitts, Streptococcus pyogenes, Staphylococcus aureus*, and *Actinomyces* species. The inhibitory factor inhibited 124 of 125 *S. mutans* strains tested. Gram-negative bacteria were mostly resistant to inhibition by mutacin 1140. The following table summarizes the spectrum of activity found for the lantibiotic. Partially purified mutacin 1140 had the same spectrum of activity displayed by JH1140, as demonstrated by spotting 5 μl samples on lawns of target strains prepared as described above. This is also shown in table 1.

TABLE 1

Mutacin Sensitivity Assay[a]

| Species | Target Strain | Test Strains JH1140 | Strain JH1005 |
|---|---|---|---|
| Mutans *Streptococci* | FA1(a) | + | +/− |
| | BHT-2(b) | + | + |
| | LM7(e) | + | + |
| | Ingbritt(c) | + | + |
| | MT-3(c) | + | + |
| | 10449(c) | + | + |
| | JC2(c) | + | + |
| | GS5(c) | + | + |
| | PK1(c) | + | + |
| *Streptococcus salivarius* | SS2 | + | + |
| | O2 | + | + |
| | O4 | + | + |
| *Streptococcus sanguis* | Fc-1 | + | + |
| | KJ3 | + | + |
| | Challis | − | + |
| *Streptococcus mitis* | MT | + | + |
| | RE-7 | + | + |
| | 26 | + | + |
| *Streptococcus pyogenes* | STA628 | + | + |
| *Streptococcus faecalis* | RF | − | ND[b] |
| *Streptococcus aureus* | DC3 | + | + |
| *Lactobacillus casei* | Lac-6 | − | + |
| *Lactobacillus salivarius* | UCL-37 | + | ND |
| *Actinomyces israelii* | X523 | + | ND |
| | 10048 | + | ND |

TABLE 1-continued

Mutacin Sensitivity Assay[a]

| Species | Target Strain | Test Strains JH1140 | Strain JH1005 |
|---|---|---|---|
| *Actinomyces naeslundii* | 12104 | + | + |
| | N16 | + | + |
| | 6-60B | + | + |
| *Actinomyces viscosus* | W1528 | + | ND |
| | T6 | + | ND |
| | M100 | + | ND |
| *Micrococcus luteus* | 207-79 | − | ND |
| *Bacteroides gingivalis* | 381 | − | ND |
| *Wolinella recta* | 371 | − | ND |
| *Capnocytophaga sputigena* | 4 | − | ND |

[a]Sensitivity to mutacin was determined as described. Indicator strains were evaluated as sensitive (+) showing zones of 10–15 mm in diameter, insensitive(−), or slightly sensitive(+/−) with zones <5 mm in diameter to test strain.
[b]Not done.

The lantibiotic's effect on other strains of *S. mutans* was bacteriocidal, since loopfuls of agar taken from clear zones were found to be sterile.

EXAMPLE 4

Characterization of Lantibiotic Peptides

Information on the total number of modified amino acids in a lantibiotic can be determined by a combination of a chemical derivatization and electrospray ionization mass spectroscopy. Edman degradation of ethane thiol-derivatized mutacin 1140 gave the results shown in the following table. This procedure was performed as described by Mezer et al., (1994) Analyt. Biochem. 223:185–190.

TABLE 2

Edman Sequencing of Mutacin 1140 Derivatized with Ethanethiol

| Cycle | Predicted Residue | Identified Residue |
|---|---|---|
| 1 | Phe | Phe |
| 2 | lys | lys |
| 3 | ser | S--EC[a] |
| 4 | trp | trp |
| 5 | ser | S--EC |
| 6 | leu | leu |
| 7 | cys | S--EC |
| 8 | thr | β-M--S--EC[a] |
| 9 | pro | pro |
| 10 | gly | gly |
| 11 | cys | S--EC |
| 12 | ala | ala |
| 13 | arg | arg |
| 14 | thr | β-M--S--EC |
| 15 | gly | gly |
| 16 | ser | S--EC |
| 17 | phe | phe |
| 18 | asn | asn |
| 19 | ser | S--EC |
| 20 | tyr | tyr |

TABLE 2-continued

| 21 | cys | ND[b] |
|---|---|---|
| 22 | cys | ND |

[a]Thioethyl cysteine (S--EC) and methylthioethyl cysteine (M--S--EC) derived from ethanethiol derivatization of lanthionine (Lan), 3methyllanthionine (MeLan), 2,3didehydroalanine (Dha) and 2,3didehydro-2-aminobutyric acid (Dhb) according to the scheme of Myers a presented below:

```
       Melan or Lan                              Dha             Dhb
---NH—CH—CO---NH—CH—CO---NH—CH—CO---NH—CH—CO----
      |            |           ||              ||
   CH3—CH——S——CH2          CH2         CH3—CH

↓ HO—CH2—CH2—SH

β-M-S-EC                          S-EC    β-M-S-EC
----NH—CH—CO---NH—CH—CO---NH—CH—CO---NH—CH—CO----
      |            |           |            |
   CH3—CH         CH2          CH2        CH3—CH
   (H) |           |            |            |
       S           SH           S            S
       |                        |            |
       CH2                      CH2          CH2
       |                        |            |
       CH2                      CH2          CH2
       |                        |            |
       OH                       OH           OH
and
                   S-EC         S-EC       β-M-S-EC
----NH—CH—CO---NH—CH—CO---NH—CH—CO---NH—CH—CO----
      |            |           |            |
   CH3—CH         CH2          CH2        CH3—CH
   (H) |           |            |            |
       SH          S            S            S
                   |            |            |
                   CH2          CH2          CH2
                   |            |            |
                   CH2          CH2          CH2
                   |            |            |
                   OH           OH           OH
```

[b]Not detected.

These analyses suggested the chemical structure shown in SEQ ID NO: 5. However, a more extensive investigation into the structure presented in Example 5 revealed that the structure is as shown in SEQ ID NO:6.

EXAMPLE 5

Further characterization of Lantibiotic Peptides

Ethanethiol derivatization. A 10 μM solution of mutacin 1140 in 100 μl of water was loaded into a prosorb column (Perkin-Elmer), and the peptide was drawn onto a poly (vinylidene difluoride) PVDF membrane. The ethanethiol derivatization method has been described in (Meyer et al., Anal. Biochem. 223:185–190 (1994)). Briefly, after the PVDF membrane had dried, 15 μl of Solution A (280 μl methanol, 200 μl water, 65 μl M sodium hydroxide, 60 μl ethanethiol (Aldrich)) was directly added to the PVDF membrane in the prosorb column. The prosorb column was then placed inside a 1.5 ml eppendorf tube, wrapped tightly with parafilm, and incubated at 50° C. for 1 h. The sample was stored for less than one day at 4° C. before sequencing.

Double labeling by sodium borohydride and ethanethiol derivatization. A 200 μM solution of mutacin 1140 in 5 μl water was added to a 0.5 ml eppendorf tube that contained 2.0 mg of sodium borohydride. This was followed by the addition of 94 μl of solution B (570 mg guanidine HCl 100 μl N-ethylmorpholine and water to a final volume of 1 ml; the pH of the mixture was adjusted to 8.5 with glacial acetic acid). The reaction mixture was then added to a vial that was purged with nitrogen gas, and incubated at 37° C. for three days. At the end of the incubation period the sample was loaded into a prosorb column (PerkinElmer), and the peptide was drawn onto a PVDF membrane. The peptide was then modified with ethanethiol as described above.

Edman sequencing procedure of mutacin 1140. A glass fiber filter was pretreated with polybrene to reduce the loss of peptide during each cycle. Precycles of the actual Edman cycles were used to wash the polybrene treated glass fiber filter. The PVDF membrane was then excised from the prosorb column and dried with nitrogen gas until it turned white. The PVDF membrane was placed into the sequencer cartridge with the polybrene treated glass fiber filter. The cartridge was then placed into the sequencer (Applied Biosystems 494 Protein P.W. Biosystems, Forster City, Calif., USA), which was operated under normal pulse-liquid blot cycles. Analysis of the amino-acid sequence was done using the ABI 610A data software. Commercially available D,L-2-aminobutyric acid (Abu) (Aldrich) was used as a standard to identify the retention time using modified cycles. To prevent Abu from completely washing off the glass fiber filter, the normal pulsed-liquid blot cycles were modified to remove all of the solvent washing steps.

Chemical Sequencing. Treatment of lantibiotic by ethanethiol results in the saturation of 2,3-didehydralanine (Dha) and 2,3-didehydrobutyrine (Dhb) residues and in the opening of thioether rings (Meyer et al.). Subsequent Edman sequencing yields an amino acid sequence with uncertain identification of dehydrated and thioether residues (for example, see FIG. 1A) (Hillman et al., Infect. Immunol. 66:2743–2749 (1998)). In order to discriminate between unsaturated amino acids and residues that form thioether rings, a double-labeling protocol was developed. The double bonds were first hydrogenated and the thioether linkages were subsequently reduced with ethanethiol. Double-labeling of mutacin 1140 yielded thioethyl cysteine residues at amino-acid positions 3, 7, 11, 16 and 19 and a 2-methylthioethyl cysteine residue at position 8. Alanine and Abu residues were formed at positions 5 and 14, respectively, from the initial hydrogenation. Thus, double labeling of mutacin 1140 provided definitive assignments of both the dehydrated amino acids, and the residues involved in thioether bridges (FIG. 1B).

Mass spectrometry. A purified sample of mutacin 1140 was analyzed by electro-spray ionization mass spectrometry (ESI-MS) and tandem mass spectrometry (MS/MS) on a PE Sciex API III Biomolecular mass analyzer (Novak et al., *Anal. Biochem.* 236:358–360 (1996)).

A vacuum dried sample of mutacin 1140 was chemically modified with 2-mercaptoethanol following the procedure described by Meyer et al under alkaline conditions. Thus, the peptide had 2-mercaptoethanol added to all of the post-translationally modified residues. A modification system was developed using 2-mercaptoethanol under neutral pH that selectively labeled only existing dehydrated residues while thioether bridges were not disrupted. A 1 mM solution of mutacin 1140 was incubated in 12 $\mu$l of 0.1 M ammonium acetate puffer pH 7 with 3 $\mu$l 2-mercaptoethanol at 50° for 1 h. Samples were then analyzed by ESI-MS and MS/MS. Mutacin 1140 was incubated for various periods of time (from 1 hour to overnight) with sequencing grade trypsin (Sigma) in 0.1 ammonium acetate buffer pH7 or phosphate buffer pH 7, and the sample was then analyzed by ESI-MS and MS/MS.

Deriviatization with 2-iminothiolane (Bartlett et al, *Biol. Mass. Spectrom.* 23:353–356 (1994)) was conducted to selectively label the N-terminal amino acid and lysine residue, allowing definitive identification of the b-series of ions derived from mutacin 1140 in the MS/MS spectra among daughter ions.

Purified mutacin 1140 was analyzed by ESI-MS and MS/MS. The calculated mass of 2263 Da was identical to that measured for mutacin 1140 in crude preparations (Hillman et al.) and indicated complete post-translational modifications. MS/MS of the doubly charged molecular ion yielded a complex spectrum of daughter ions. The major ion was the doubly charged molecular ion, indicating the noteworthy stability of the peptide. The spectra had ions with the loss or addition of approximately 32 or 33 mass units, suggesting the loss or addition of S or SH atoms involved with thioether linkages. The interpretation of the b-ions was supported by an additional experiment in which the N-terminal portion (N-terminus and lysine residue) was labeled with 2-iminothiolane (Bartlett et al., *Biol. Mass Spectrom.* 23:353–356 (1994)), and the doubly charged molecular ion with two additions (to the first two N-terminal amino acid residues, Phe and Lys) was subjected again to collision-induced dissociation. The corresponding increases in masses confirmed the identity of b-ions.

These results, together with an almost complete series of b-ions and y-daughter ions indicated that thioether bonds break during collision-induced dissociation in ESI-MS/MS. Tandem mass spectrometry of a lanthionine standard indicated that the major daughter ions were generated by breaking the thioether bonds, confirming the interpretation of the mutacin 1140 data.

To detect dehydrated residues, a reaction was developed with 2-mercaptoethanol at neutral pH that selectively labeled these groups. This chemical modification resulted in reaction products, detected in the ESI-mass spectra, that contains additions of one, two, and three molecules of 2-mercaptoethanol. This was consistent with two dehydrated residues and an S-[aminovinyl]-cysteine (Hillman et al.). The amount of the fully derivatized molecule with three additions was not sufficient for tandem mass spectrometry, but mutacin 1140 with one and two additions were subjected to collision-induced dissociation with good results. Daughter ions of the doubly charged molecule of mutacin 1140 with two additions or 2-mercaptoethanol were determined. The 2-mercaptoethanol added 78 and 156 mass units to all b-ions following positions 5 and 14, respectively, demonstrating that these residues are Dha5 and Dhb14. The y-ion series gave similar results. Interestingly, the MS/MS spectra of mutacin 1140 indicated that a single 2-mercaptoethanol addition was localized in Dha5. This suggested good accessibility or higher reactivity of this residue compared to the other two available sizes (Dhb 13, Av22).

The absence of secondary daughter ions derived from b-ions or y-ions by loss or addition of S or SH atoms in the Ala12-Gly15 region suggested that there are no thioether bridges crossing over this region. Therefore, mutacin 1140 could be cleaved by trypsin after the Arg 13 residue to yield two fragments, as described for gallidermin (Kellner et al., *Eur. J. Biochem.* 177:53–59 (1988)). Mutacin 1140 tryptic digest were generated using both soluble and immobilized sequence-grade trypsin with identical results. We observed a 1401 Da peptide that was identified by tandem mass spectrometry as the N-terminal fragment Phe1-Arg13. The C-terminal fragment was not detected, probably due to the deamination of Dhb 14 after the cleavage (similar to epidermin and gallidermin (Kellner et al.)). In contrast to intact mutacin 1140, collision-induced dissociation of the N-terminal tryptic fragment yielded a spectrum in which the doubly charged parent ion (m/z 701) was detected but was not a major signal. Apparently, structural features responsible for the remarkable stability of the mutacin 1140 peptide requires an intact molecule, and are likely a result of the conformation of the whole molecule, and not just the thioether bridges in the cleaved fragment.

NMR Spectroscopy

Mutacin 1140 is not soluble in aqueous solutions at concentrations required for NMR. Therefore, 2mM samples of mutacin 1140 were prepared in 70–90% acetonitrile-$d_3$ (Cambridge Isotopes) and 10–30% water in a total volume of 700 $\mu$l. The NMR data were collected on Varian Unity and Bruker Advance spectrometers, both operating at a proton frequency of 600 MHz. The $^1$H resonances were assigned according to standard methods (Wuthrich, (1986) NMR of Proteins and Nucleic Acids. Wiley, New York) using TOCSY (Braunschweiler & Ernst, *J. Magn. Reson.* 53:521–528 (1983)) and NOESY (Kumar et al., *Biochem. Biophys. Res. Comm.*, 95:1–6 (1980) experiments. HMQC (Muller, *J. Am. Chem. Soc.* 101:4481–4484 (1979), Bax et al. *J. Magn. Reson.* 55: 301–315 (1983) and HMBC (Bax & Summers, *J. Am. Chem. Soc.* 108:2093–2094 (1986)) experiments were used to clarify some areas of ambiguity in the TOCSY and NOESY spectra. NMR experiments were collected at 25° C. and the carrier frequency was centered on the water resonance, which was suppressed by presaturation during the 1.5s relaxation delay. The TOCSY experiments were acquired with a 60 ms mixing time using the MLEV-17 sequence (Bax & Davis, *J. Magn. Reson.* 65:355–360 (1985)). The NOESY experiments were acquired with 200 ms, 400 ms, and 450 ms mixing times. The delay times to create or refocus antiphase coherence in the HMQC and HMBC were 8000.0 Hz (13.3 p.p.m.) in the proton dimensions and 22500.0 Hz (149.1 p.p.m.) and 30000.0 Hz (198.9 p.p.m.) for the carbon dimensions, respectively. All 2D data were collected with 2048 complex points in the acquisition dimension and between 256 and 512 complex points for the indirect dimensions. Phase sensitive indirect detection for all experiments was achieved using the method of States-TPPI (Marion et al., J. Magn. Reson. 85:393–399 (1989)). $^1$H chemical shifts were referenced to acetonitrile (1.93 p.p.m.). Data were processed with NMRpipe (Delaglio et al., J. Biomol. NMR 6: 277–293 (1995)) by first removing the residual water signal by deconvolution, multiplying the data in both dimension by a squared cosine function or a squared cosine function with a 60° shift (for the $^1$H dimension of HMBC), zerofilling once, Fourier transformation, and baseline correction. Data were analyzed with the interactive computer program NMRview (Johnson & Blevins, J. Biolmol. NMR 4:603–614 (1994)).

NMR is clearly the definitive method for complete lantibiotic structure determination (van de Ven & Jung, Antonie Van Leeuwenhoek, 69:99–107 (1996)). Therefore, in order both to verify the double-labeling result and to firmly establish the correct thioether pairings, we collected TOCSY, NOESY, HMQC, and HMBC NMR data on mutacin 1140. The TOSCY/NOESY data sets provided unambiguous sequential assignments, so the HMQC/HMBC data sets were primarily used as supporting evidence to the proton-based assignments. Based on distinct spin systems 21 amino acids and one aminovinyl group were identified in the TOCSY and NOESY experiments. Unmodified amino acids were sequentially assigned by standard methods (Suhl et al., Eur. J. Biochem. 230:827–853 (1995)) and agreed perfectly with the known mutacin 1140 prepropeptide sequence (Hillman et al.).

Residues 2 through 4 were identified through an $H^\alpha_1$ to $H^N_{i+1}$ sequential walk. The residue at position 3 has a chemical shift pattern characteristic of an alanyl moiety of lanthionine and 2-methyl-lanthionine ($Ala_s$). Distinct vinyl proton chemical shifts, consistent with a Dha, have strong NOEs to the amide proton of Leu 6. The HMBC spectrum provided additional correlations between the Dha vinyl protons to the Leu 6 $H^N$ by way of the Dha $C^1$ resonance, verifying that the amino acid at position 5 is a Dha residue. Leu 6 has several $H^\alpha$ and side-chain proton NOEs to $H^N$ of $Ala_s$ at position 7, which in turn has $H^N$ to $H^\beta$ and $H^\beta$ to $H^\beta$ NOEs to $Ala_s$ 3. Thus, amino acid 5 is a Dha and amino acids at positions 3 and 7 form a lanthionine. Several NOEs, including $H^\alpha_1$ to $H^N_{i+1}$, exist between $Ala_s$ 7 and the amide proton of a spin system consistent with 2-methyl-ananyl moiety of 2-methyl-lantionine ($Abu_s$), which in turn has an $H^\alpha$ to $H^\delta$ NOE to Pro9 and establishes a trans AbuS-Pro peptide bond. A complete sequential walk could be made between residues 10 and 14. Chemical shift patterns and an $H^\alpha_1$ to $H^N_{i+1}$ NOE from Gly10 indicate that position 11 is $Ala_s$. Sequential $H^N$ NOEs correlate amino acids 14 through 16, and a spin system characteristic of a Dhb residue is between Arg 13 and Gly15. Several NOEs between $Abu_s8$ and $Ala_s11$, including $H^\beta$ to $H^\beta$ and $H^\gamma$ to $H^\beta$, show that these residues form a thioether bridge. Thus, amino acids 8 and 11 form a 2-methyl-lanthionine and the amino acid at position 14 is a Dhb.

A sequential $H^\alpha_i$ to $H^N_{i+1}$ walk could be made from residues 16 through 18. Chemical shifts and several NOEs between Gly 15 and Phe 17 indicate that position 16 is $Ala_s$. A sequential walk could be made from residues 19 through 21. The residue following Tyr20 is $Ala_s21$, which in turn has $H^\beta$ to $H^\beta$ and $H^\beta$ to $H^N$ NOEs to $Ala_s16$, verifying a thioether bridge between $Ala_s$ 16 and 21. Another $Ala_s$ residue was similarly identified at position 19. $Ala_s$ 21 has sequential NOEs to a spin system characteristic of an amino vinyl group, which in turn has vinyl proton to $H^{\alpha\beta}$ NOEs to $Ala_s$ 19. Thus, amino acid 16 and 21 form a lanthionine, and residue 19 and the C-terminal amino vinyl group form an S-[aminovinyl]-cysteine. The complete structure of mutacin 1140 is shown in FIG. 1C.

All of the data (chemical, mass spectrometry, and NMR) presented above are in complete agreement and support the structure of mutacin 1140 shown in SEQ ID NO:6. The chemical modification and mass spectrometry data were able to unambiguously distinguish between residues that are dehydrated or involved in thioether linkages. The NMR data verified these assignments and also allowed of the specific identification of 2-methyl-lanthionine and lanthionine residues through inter-residue NOEs. The structure of mutacin is also consistent with similar type A lantibiotics such as gallidermin (Kellner et al. Eur. J. Biochem. 177:53–59 (1988); van de Ven & Jung, Antonie Van Leeuwenhoek, 69:99–107 (1996), Freund et al., Biopolymers, 6:803–811 (1991)), and epidermin (Schnell et al., Nature, 333:276–278 (1988)). This is in contrast to the preliminary structure, which proposed different thioether bridging patterns.

While amino-acid sequence homology to other lantibiotics provides strong evidence for homologous thioether bridging, it cannot confirm that this bridging occurs (Bierbaum et al., Appl. Environ. Microbiol. 62:385–392 (1996), Karakas et al., Eur. J. Biochem., 261-524–532 (1999)). Despite the fact that mutacin 1140 has significant sequence similarity to other lantibiotics, misinterpretation of initial experimental results led to the proposal of a nonhomologous structure (SEQ ID NO:5).

EXAMPLE 6

Genetic Analysis

A genetic analysis of a strain producing the lantibiotic was performed. The analysis utilized a plasmid pTV1-OK which is a repA (ts) derivative of the *Lactococcus lactis* cryptic plasmid pWV01 for temperature-dependent replication in both *S. mutans* and *Escherichia coli*. The plasmid possesses the transposon Tn917, which confers erythromycin resistance in streptococci. Transposon mutagenesis was performed on lantibiotic-producing strain JH1005 harboring pTV1-OK. Erythromycin resistant clones were selected on BHI agar using 15 µg/ml antibiotic and were then stab inoculated into the same medium without antibiotic. After incubation overnight in candle jars at 37° C., the plates were overlaid with 3 ml of top agar containing about $10^6$ colony forming units per ml of BHT-2. Stabbed clones which failed to produce growth inhibition of the BHT-2 lawn were recovered and purified by streaking on a medium with erythromycin.

From these mutants, which now had the transposon in the genetic elements responsible for lantibiotic production, chromosomal DNA was isolated and DNA flanking the Tn917 insert was cloned into *E. coli* strain MC 1061. The flanking DNA was sequenced by the University of Florida ICBR using Taq Dye Deoxy Terminator and Dye Primer Cycle Sequencing protocols as published by Applied Biosystems, using an Applied Biosystems Model 373A DNA Sequencer. Homology searches were conducted on the recovered sequences using the BLAST program. The recovered sequences, designated lanA and lanB are presented as SEQ ID NO:1 and SEQ ID NO:3 below. These sequences were found to have homology to epiA and epiB. The open reading frames of these DNA sequences produce the proteins presented in SEQ ID NO:2 and SEQ ID NO:4.

What is claimed is:

1. An isolated lantibiotic comprising SEQ ID NO:6.

2. An isolated lantibiotic comprising the following structure:

SEQ ID NO:6

F—K—A—W—Dha—L—A—Abu—P—G—A—A—R—Dhb—G—A—F—N—A—Y—A with S bridges and terminal ring structure containing S, C=C, NH, H, H 3. The isolated lantibiotic of claim 1, wherein a single conservative amino acid substitution occurs either at amino acid position 1, 2, 4, 5, 6, 13, or 19.

4. The isolated lantibiotic of claim 1, wherein a conservative amino acid substitution occurs at amino acid number 13, and comprises a Lys in place of an Arg (SEQ ID NO:7).

5. The isolated lantibiotic of claim 1, wherein a conservative amino acid substitution occurs at amino acid number 19 and comprises a Dha in place of an Ala (SEQ ID NO:8).

6. The isolated lantibiotic of claim 1, wherein a conservative substitution occurs at amino acid number 6 and comprises a Phe in place of a Leu (SEQ ID NO:9).

7. The isolated lantibiotic of claim 1, wherein the lantibiotic comprises:
   (a) an amino acid substitution at amino acid number 6, which comprises a Phe in place of a Leu; and
   (b) an amino acid substitution at amino acid number 13, which comprises a Lys in place of an Arg; which is shown in SEQ ID NO:11.

8. A detrifrice comprising the isolated lantibiotic of claim 1 and a carrier or excipient.

9. A bacteriocidal or bacteriostatic composition comprising an effective amount of the lantibiotic of claim 1 and a carrier or excipient.

10. A bacteriocidal or bacteriostatic composition comprising an effective amount of the lantibiotic of claim 7 and a carrier or excipient.

11. A pharmaceutical composition comprising the lantibiotic of claim 1 and a pharmaceutically acceptable carrier or excipient.

12. A pharmaceutical composition comprising the lantibiotic of claim 7 and a pharmaceutically acceptable carrier or excipient.

13. The pharmaceutical composition of claim 11, wherein the lantibiotic is active against a Gram positive bacteria.

14. The pharmaceutical composition of claim 13, wherein the Gram positive bacteria is selected from the group consisting of *Actinomyces, Bacillus, Clostridium, Corynebacterium, Enterococcus, Listeria, Lactobacillus, Mycobacterium, Propionobacteria, Staphylococci,* and *Streptococci*.

15. The pharmaceutical composition of claim 13, wherein the Gram positive bacteria is selected from the group consisting of *Corynebacterium diphtheriae, Propionobacterium acnes, Listeria monocytegenes, Bacillus anthracis,* and *Mycobacterium phlei*.

16. The pharmaceutical composition of claim 13, wherein the lantibiotic is active against a Gram negative bacteria.

17. The pharmaceutical composition of claim 13, wherein the Gram negative bacteria is selected from the group consisting of *Flavobacterium, Actinobacillus, Enterobacter,* and *Neisseria*.

18. A pharmaceutical composition comprising a bacteriostatic or bacteriocidal amount of the lantibiotic of claim 1 and a carrier or excipient.

19. A pharmaceutical composition comprising a bacteriostatic or bacteriocidal amount of the lantibiotic of claim 7 and a carrier or excipient.

* * * * *

SEQUENCE LISTING

<160> NUMBER OF SEQ ID NOS: 12

<210> SEQ ID NO 1
<211> LENGTH: 1316
<212> TYPE: DNA
<213> ORGANISM: Streptococcus mutans
<220> FEATURE:
<221> NAME/KEY: CDS
<222> LOCATION: (796)..(987)
<223> OTHER INFORMATION:
<221> NAME/KEY: -35_signal
<222> LOCATION: (738)..(742)
<223> OTHER INFORMATION:
<221> NAME/KEY: -10_signal
<222> LOCATION: (757)..(763)
<223> OTHER INFORMATION:
<221> NAME/KEY: RBS
<222> LOCATION: (784)..(791)
<223> OTHER INFORMATION:

<400> SEQUENCE: 1

```
aatctatttt gtagagaatt tagagaaatt attaaattac caagatatgt ttgcaataac     60 attttttaaaa tttttaaaaa aaattattac ttactttcat gataagtcag tagatatgtc    120
tgaattagaa cattatatta atatagttga agaaataaat cctacgattg cttcaattct    180
taaatctaat ttgaatcagc ttttataaag ttttagccat taaagccatc ttgataaatt    240
ttatatcttt catattcatt aaatgtggag ataatgaaaa agcaacggtt atgctatcgc    300
tgcttttttt gtgattagaa gctatgttat catggagtta tagtaatgaa acatagtgac    360
agttcatcct ttcttattat aaaagtggta ataagagaag tggtaaacaa agagttagta    420
aaataatacg tttaaccata atatttcctc ctttaattta ttataagatt caaaaaggta    480
atattcctat atttgcaaat atgggataaa ataattttaa aaaagcagat ttgcaatttt    540
aaaaaaatag aggctaatgg tggtattata ttattgtaaa tatatgttta ctcagtaata    600
gtgatttact attacaacag attttgttgt tatcttagat atttctgcta gcattagtta    660
tctgtagatg tactacttaa taagtatata attataatta tataataact attatcagat    720
taccgttaaa agttttctga tatgcttcta ctgaacaatt tatgttcagt tacacacatg    780
aaaaaggagg atatt atg tca aac aca caa tta tta gaa gtc ctt ggt act     831
                 Met Ser Asn Thr Gln Leu Leu Glu Val Leu Gly Thr
                   1               5                  10 gaa act ttt gat gtt caa gaa gat ctc ttt gct ttt gat aca aca gat     879
Glu Thr Phe Asp Val Gln Glu Asp Leu Phe Ala Phe Asp Thr Thr Asp
         15                  20                  25 act act att gtg gca agc aac gac gat cca gat act cgt ttc aaa agt     927
Thr Thr Ile Val Ala Ser Asn Asp Asp Pro Asp Thr Arg Phe Lys Ser
     30                  35                  40 tgg agc ctt tgt acg cct ggt tgt gca agg aca ggt agt ttc aat agt     975
Trp Ser Leu Cys Thr Pro Gly Cys Ala Arg Thr Gly Ser Phe Asn Ser
 45                  50                  55                  60 tac tgt tgc tga ttgtataaaa gatttagatt gtgccgcatg ttagcggcac         1027
Tyr Cys Cys aatcttttga tattagaggt attaatatgt taaatacaca attattagaa gtccttggta   1087
ctaaaacttt tgatgttcaa gaagatttat ttgagtttaa tataacagat actattgtac   1147
tgcaggctag tgatagtcca gatactcata gtaggggtcc cgagcgctta gtgggaattt   1207
gtatcgataa ggggtacaaa ttcccactaa accaatgttt caaggcctat ttattttta    1267 tattcaattc tcttaagtgt ttaggaatag ataacaagtc aaatttata               1316
```

<210> SEQ ID NO 2
<211> LENGTH: 63
<212> TYPE: PRT
<213> ORGANISM: Streptococcus mutans

<400> SEQUENCE: 2

```
Met Ser Asn Thr Gln Leu Leu Glu Val Leu Gly Thr Glu Thr Phe Asp
1               5                   10                  15

Val Gln Glu Asp Leu Phe Ala Phe Asp Thr Thr Asp Thr Thr Ile Val
            20                  25                  30

Ala Ser Asn Asp Asp Pro Asp Thr Arg Phe Lys Ser Trp Ser Leu Cys
        35                  40                  45

Thr Pro Gly Cys Ala Arg Thr Gly Ser Phe Asn Ser Tyr Cys Cys
    50                  55                  60
```

<210> SEQ ID NO 3
<211> LENGTH: 1323
<212> TYPE: DNA
<213> ORGANISM: Streptococcus mutans
<220> FEATURE:
<221> NAME/KEY: CDS
<222> LOCATION: (228)..(782)
<223> OTHER INFORMATION:
<221> NAME/KEY: -35_signal
<222> LOCATION: (177)..(182)
<223> OTHER INFORMATION:
<221> NAME/KEY: -10_signal
<222> LOCATION: (191)..(196)
<223> OTHER INFORMATION:
<221> NAME/KEY: RBS
<222> LOCATION: (218)..(224)
<223> OTHER INFORMATION:

<400> SEQUENCE: 3

```
tagtaaagtg ggtagtttca atatctgccc tcctcgaaag atctccgtca gtttcaatag      60
ttactgttgt taactataaa ttatacttaa attgatagga aacttggtcg tgacattatc     120
atatgttgat attggaagag aatcaaattt ataaagacaa ttaaatctaa atttgatgaa     180
tatttagatg aattattact aggttgacag tcatgttagg agaagag atg aac gat        236
                                                 Met Asn Asp
                                                  1 ttt caa ttt caa gat tat ttt atg tac aga aaa cca tta ggc aac ttt       284
Phe Gln Phe Gln Asp Tyr Phe Met Tyr Arg Lys Pro Leu Gly Asn Phe
    5                   10                  15 tct aat ttt ttt agt ata act gat acg atg gat ccc att gag tta cta       332
Ser Asn Phe Phe Ser Ile Thr Asp Thr Met Asp Pro Ile Glu Leu Leu
20                  25                  30                  35 cat agt gat ccg ata ttt gct gaa gga gta tat ttg gcc tct tca tct       380
His Ser Asp Pro Ile Phe Ala Glu Gly Val Tyr Leu Ala Ser Ser Ser
                40                  45                  50 ctt aga gca gcc ata aat aaa ctt aag aat cat act gcg agt act aag       428
Leu Arg Ala Ala Ile Asn Lys Leu Lys Asn His Thr Ala Ser Thr Lys
            55                  60                  65 gat aaa aag aat gca aga gag act att ttt caa tac tat gcc cgt tat       476
Asp Lys Lys Asn Ala Arg Glu Thr Ile Phe Gln Tyr Tyr Ala Arg Tyr
        70                  75                  80 aac acg aga tca act ccg ttt ggc ttg ttt tcg tcc atc gga gta ggt       524
Asn Thr Arg Ser Thr Pro Phe Gly Leu Phe Ser Ser Ile Gly Val Gly
    85                  90                  95 gct ttt tcg gct tac ctt aaa aaa gaa aag tct cgt tat gaa aaa tct       572
Ala Phe Ser Ala Tyr Leu Lys Lys Glu Lys Ser Arg Tyr Glu Lys Ser
100                 105                 110                 115
```

```
att aat att gat ctt ttt tgg gct tat aaa gta gca gat aaa cta gaa        620
Ile Asn Ile Asp Leu Phe Trp Ala Tyr Lys Val Ala Asp Lys Leu Glu
            120                 125                 130 agt atg cct gaa att tta aat act tta aaa gta gtt gct aat aat gct        668
Ser Met Pro Glu Ile Leu Asn Thr Leu Lys Val Val Ala Asn Asn Ala
        135                 140                 145 ttg caa aag tca gat aat ttt tgg ctt ttg gat acg cga agt cat ttt        716
Leu Gln Lys Ser Asp Asn Phe Trp Leu Leu Asp Thr Arg Ser His Phe
    150                 155                 160 ggt ctt atg aat tct ttt cat ttt atc ttg tac gac ttc tat tct ttc        764
Gly Leu Met Asn Ser Phe His Phe Ile Leu Tyr Asp Phe Tyr Ser Phe
165                 170                 175 ctt caa gat aga cca taa gaattgatat atcagctgga ttcacaccag                812
Leu Gln Asp Arg Pro
180 aaatacggct agcttgacca atagtttctg ggttaatttt cttaaatttc tgacgtgctt       872 cggtcgcaat agaatcaatg gcatcccaat cgatattctt aggaattcga gctcggtacc       932 cggggatcct ctagagtcga cctgcaggca tgcaagcttg gcactggccg tcgttttaca       992 acgtcgtgac tgggaaaacc ctggcgttac ccaacttaat cgccttgcag cacatccccc      1052 tttcgccagc tggcgtaata gcgaagaggc ccgcaccgat cgcccttccc aacagttgcg      1112 cagcctgaat ggcgaatggc gcctgatgcg gtattttctc cttacgcatc tgtgcggtat      1172 ttcacaccgc atatggtgca ctctcagtac aatctgctct gatgccgcat agttaagcca      1232 gccccgacac ccgccaacac ccgctgacgc gccctgacgg gcttgtctgc tcccggcatc      1292 cgcttacaga caagctgtga ccgtctccgg g                                     1323

<210> SEQ ID NO 4
<211> LENGTH: 184
<212> TYPE: PRT
<213> ORGANISM: Streptococcus mutans

<400> SEQUENCE: 4

Met Asn Asp Phe Gln Phe Gln Asp Tyr Phe Met Tyr Arg Lys Pro Leu
1               5                   10                  15

Gly Asn Phe Ser Asn Phe Phe Ser Ile Thr Asp Thr Met Asp Pro Ile
            20                  25                  30

Glu Leu Leu His Ser Asp Pro Ile Phe Ala Glu Gly Val Tyr Leu Ala
        35                  40                  45

Ser Ser Ser Leu Arg Ala Ala Ile Asn Lys Leu Lys Asn His Thr Ala
    50                  55                  60

Ser Thr Lys Asp Lys Lys Asn Ala Arg Glu Thr Ile Phe Gln Tyr Tyr
65                  70                  75                  80

Ala Arg Tyr Asn Thr Arg Ser Thr Pro Phe Gly Leu Phe Ser Ser Ile
                85                  90                  95

Gly Val Gly Ala Phe Ser Ala Tyr Leu Lys Glu Lys Ser Arg Tyr
            100                 105                 110

Glu Lys Ser Ile Asn Ile Asp Leu Phe Trp Ala Tyr Lys Val Ala Asp
        115                 120                 125

Lys Leu Glu Ser Met Pro Glu Ile Leu Asn Thr Leu Lys Val Val Ala
    130                 135                 140

Asn Asn Ala Leu Gln Lys Ser Asp Asn Phe Trp Leu Leu Asp Thr Arg
145                 150                 155                 160

Ser His Phe Gly Leu Met Asn Ser Phe His Phe Ile Leu Tyr Asp Phe
                165                 170                 175
```

-continued

```
Tyr Ser Phe Leu Gln Asp Arg Pro
            180

<210> SEQ ID NO 5
<211> LENGTH: 22
<212> TYPE: PRT
<213> ORGANISM: Streptococcus mutans
<220> FEATURE:
<221> NAME/KEY: MISC_FEATURE
<222> LOCATION: (3)..(3)
<223> OTHER INFORMATION: 2,3-didehydroalanine
<221> NAME/KEY: MISC_FEATURE
<222> LOCATION: (5)..(5)
<223> OTHER INFORMATION: alanyl moiety of lanthionine
<221> NAME/KEY: MISC_FEATURE
<222> LOCATION: (7)..(7)
<223> OTHER INFORMATION: alanyl moiety of lanthionine
<221> NAME/KEY: MISC_FEATURE
<222> LOCATION: (11)..(11)
<223> OTHER INFORMATION: alanyl moiety of lanthionine
<221> NAME/KEY: MISC_FEATURE
<222> LOCATION: (16)..(16)
<223> OTHER INFORMATION: alanyl moiety of lanthionine
<221> NAME/KEY: MISC_FEATURE
<222> LOCATION: (19)..(19)
<223> OTHER INFORMATION: alanyl moiety of lanthionine
<221> NAME/KEY: MISC_FEATURE
<222> LOCATION: (21)..(21)
<223> OTHER INFORMATION: alanyl moiety of lanthionine
<221> NAME/KEY: MISC_FEATURE
<222> LOCATION: (8)..(8)
<223> OTHER INFORMATION: 2,3-didehydrobutyrine
<221> NAME/KEY: MISC_FEATURE
<222> LOCATION: (14)..(14)
<223> OTHER INFORMATION: S-2-aminobutyric acid
<221> NAME/KEY: MISC_FEATURE
<222> LOCATION: (22)..(22)
<223> OTHER INFORMATION: S-[aminovinyl]-cysteine
<221> NAME/KEY: THIOETH
<222> LOCATION: (5)..(7)
<223> OTHER INFORMATION:
<221> NAME/KEY: THIOETH
<222> LOCATION: (11)..(14)
<223> OTHER INFORMATION:
<221> NAME/KEY: THIOETH
<222> LOCATION: (16)..(21)
<223> OTHER INFORMATION:
<221> NAME/KEY: THIOETH
<222> LOCATION: (19)..(22)
<223> OTHER INFORMATION:

<400> SEQUENCE: 5

Phe Lys Xaa Trp Xaa Leu Xaa Xaa Pro Gly Xaa Ala Arg Xaa Gly Xaa
1               5                   10                  15

Phe Asn Xaa Tyr Xaa Xaa
            20

<210> SEQ ID NO 6
<211> LENGTH: 22
<212> TYPE: PRT
<213> ORGANISM: Streptococcus mutans
<220> FEATURE:
<221> NAME/KEY: MISC_FEATURE
<222> LOCATION: (3)..(3)
<223> OTHER INFORMATION: alanyl moiety of lanthionine
<221> NAME/KEY: MISC_FEATURE
<222> LOCATION: (5)..(5)
<223> OTHER INFORMATION: 2,3-didehydroalanine
<221> NAME/KEY: MISC_FEATURE
<222> LOCATION: (7)..(7)
<223> OTHER INFORMATION: alanyl moiety of lanthionine
<221> NAME/KEY: MISC_FEATURE
<222> LOCATION: (11)..(11)
<223> OTHER INFORMATION: alanyl moiety of lanthionine
```

```
<221> NAME/KEY: MISC_FEATURE
<222> LOCATION: (16)..(16)
<223> OTHER INFORMATION: alanyl moiety of lanthionine
<221> NAME/KEY: MISC_FEATURE
<222> LOCATION: (19)..(19)
<223> OTHER INFORMATION: alanyl moiety of lanthionine
<221> NAME/KEY: MISC_FEATURE
<222> LOCATION: (21)..(21)
<223> OTHER INFORMATION: alanyl moiety of lanthionine
<221> NAME/KEY: MISC_FEATURE
<222> LOCATION: (8)..(8)
<223> OTHER INFORMATION: S-2-aminobutyric acid
<221> NAME/KEY: MISC_FEATURE
<222> LOCATION: (14)..(14)
<223> OTHER INFORMATION: 2,3-didehydrobutyrine
<221> NAME/KEY: MISC_FEATURE
<222> LOCATION: (22)..(22)
<223> OTHER INFORMATION: S-[aminovinyl]-cysteine
<221> NAME/KEY: THIOETH
<222> LOCATION: (3)..(7)
<223> OTHER INFORMATION:
<221> NAME/KEY: THIOETH
<222> LOCATION: (8)..(11)
<223> OTHER INFORMATION:
<221> NAME/KEY: THIOETH
<222> LOCATION: (16)..(21)
<223> OTHER INFORMATION:
<221> NAME/KEY: THIOETH
<222> LOCATION: (19)..(22)
<223> OTHER INFORMATION:

<400> SEQUENCE: 6

Phe Lys Xaa Trp Xaa Leu Xaa Xaa Pro Gly Xaa Ala Arg Xaa Gly Xaa
1               5                   10                  15

Phe Asn Xaa Tyr Xaa Xaa
            20

<210> SEQ ID NO 7
<211> LENGTH: 22
<212> TYPE: PRT
<213> ORGANISM: Streptococcus mutans
<220> FEATURE:
<221> NAME/KEY: MISC_FEATURE
<222> LOCATION: (3)..(3)
<223> OTHER INFORMATION: alanyl moiety of lanthionine
<221> NAME/KEY: MISC_FEATURE
<222> LOCATION: (7)..(7)
<223> OTHER INFORMATION: alanyl moiety of lanthionine
<221> NAME/KEY: MISC_FEATURE
<222> LOCATION: (11)..(11)
<223> OTHER INFORMATION: alanyl moiety of lanthionine
<221> NAME/KEY: MISC_FEATURE
<222> LOCATION: (16)..(16)
<223> OTHER INFORMATION: alanyl moiety of lanthionine
<221> NAME/KEY: MISC_FEATURE
<222> LOCATION: (19)..(19)
<223> OTHER INFORMATION: alanyl moiety of lanthionine
<221> NAME/KEY: MISC_FEATURE
<222> LOCATION: (21)..(21)
<223> OTHER INFORMATION: alanyl moiety of lanthionine
<221> NAME/KEY: MISC_FEATURE
<222> LOCATION: (5)..(5)
<223> OTHER INFORMATION: 2,3-didehydroalanine
<221> NAME/KEY: MISC_FEATURE
<222> LOCATION: (8)..(8)
<223> OTHER INFORMATION: S-2-aminobutyric acid
<221> NAME/KEY: MISC_FEATURE
<222> LOCATION: (14)..(14)
<223> OTHER INFORMATION: 2,3-didehydrobutyrine
<221> NAME/KEY: MISC_FEATURE
<222> LOCATION: (22)..(22)
<223> OTHER INFORMATION: S-[aminovinyl]-cysteine
<221> NAME/KEY: THIOETH
<222> LOCATION: (3)..(7)
<223> OTHER INFORMATION:
<221> NAME/KEY: THIOETH
```

```
<222> LOCATION: (8)..(11)
<223> OTHER INFORMATION:
<221> NAME/KEY: THIOETH
<222> LOCATION: (6)..(21)
<223> OTHER INFORMATION:
<221> NAME/KEY: THIOETH
<222> LOCATION: (19)..(22)
<223> OTHER INFORMATION:

<400> SEQUENCE: 7

Phe Lys Xaa Trp Xaa Leu Xaa Xaa Pro Gly Xaa Ala Lys Xaa Gly Xaa
1               5                   10                  15

Phe Asn Xaa Tyr Xaa Xaa
            20

<210> SEQ ID NO 8
<211> LENGTH: 22
<212> TYPE: PRT
<213> ORGANISM: Streptococcus mutans
<220> FEATURE:
<221> NAME/KEY: MISC_FEATURE
<222> LOCATION: (3)..(3)
<223> OTHER INFORMATION: alanyl moiety of lanthionine
<221> NAME/KEY: MISC_FEATURE
<222> LOCATION: (7)..(7)
<223> OTHER INFORMATION: alanyl moiety of lanthionine
<221> NAME/KEY: MISC_FEATURE
<222> LOCATION: (11)..(11)
<223> OTHER INFORMATION: alanyl moiety of lanthionine
<221> NAME/KEY: MISC_FEATURE
<222> LOCATION: (16)..(16)
<223> OTHER INFORMATION: alanyl moiety of lanthionine
<221> NAME/KEY: MISC_FEATURE
<222> LOCATION: (21)..(21)
<223> OTHER INFORMATION: alanyl moiety of lanthionine
<221> NAME/KEY: MISC_FEATURE
<222> LOCATION: (5)..(5)
<223> OTHER INFORMATION: 2,3-didehydroalanine
<221> NAME/KEY: MISC_FEATURE
<222> LOCATION: (19)..(19)
<223> OTHER INFORMATION: 2,3-didehydroalanine
<221> NAME/KEY: MISC_FEATURE
<222> LOCATION: (8)..(8)
<223> OTHER INFORMATION: S-2-aminobutyric acid
<221> NAME/KEY: MISC_FEATURE
<222> LOCATION: (14)..(14)
<223> OTHER INFORMATION: 2,3-didehydrobutyrine
<221> NAME/KEY: MISC_FEATURE
<222> LOCATION: (22)..(22)
<223> OTHER INFORMATION: S-[aminovinyl]-cysteine
<221> NAME/KEY: THIOETH
<222> LOCATION: (3)..(7)
<223> OTHER INFORMATION:
<221> NAME/KEY: THIOETH
<222> LOCATION: (8)..(11)
<223> OTHER INFORMATION:
<221> NAME/KEY: THIOETH
<222> LOCATION: (16)..(21)
<223> OTHER INFORMATION:
<221> NAME/KEY: THIOETH
<222> LOCATION: (19)..(22)
<223> OTHER INFORMATION:

<400> SEQUENCE: 8

Phe Lys Xaa Trp Xaa Leu Xaa Xaa Pro Gly Xaa Ala Arg Xaa Gly Xaa
1               5                   10                  15

Phe Asn Xaa Tyr Xaa Xaa
            20

<210> SEQ ID NO 9
<211> LENGTH: 22
<212> TYPE: PRT
<213> ORGANISM: Streptococcus mutans
```

```
<220> FEATURE:
<221> NAME/KEY: MISC_FEATURE
<222> LOCATION: (3)..(3)
<223> OTHER INFORMATION: alanyl moiety of lanthionine
<221> NAME/KEY: MISC_FEATURE
<222> LOCATION: (7)..(7)
<223> OTHER INFORMATION: alanyl moiety of lanthionine
<221> NAME/KEY: MISC_FEATURE
<222> LOCATION: (11)..(11)
<223> OTHER INFORMATION: alanyl moiety of lanthionine
<221> NAME/KEY: MISC_FEATURE
<222> LOCATION: (16)..(16)
<223> OTHER INFORMATION: alanyl moiety of lanthionine
<221> NAME/KEY: MISC_FEATURE
<222> LOCATION: (19)..(19)
<223> OTHER INFORMATION: alanyl moiety of lanthionine
<221> NAME/KEY: MISC_FEATURE
<222> LOCATION: (21)..(21)
<223> OTHER INFORMATION: alanyl moiety of lanthionine
<221> NAME/KEY: MISC_FEATURE
<222> LOCATION: (5)..(5)
<223> OTHER INFORMATION: 2,3-didehydroalanine
<221> NAME/KEY: MISC_FEATURE
<222> LOCATION: (8)..(8)
<223> OTHER INFORMATION: S-2-aminobutyric acid
<221> NAME/KEY: MISC_FEATURE
<222> LOCATION: (14)..(14)
<223> OTHER INFORMATION: 2,3-didehydrobutyrine
<221> NAME/KEY: MISC_FEATURE
<222> LOCATION: (22)..(22)
<223> OTHER INFORMATION: S-[aminovinyl]-cysteine
<221> NAME/KEY: THIOETH
<222> LOCATION: (3)..(7)
<223> OTHER INFORMATION:
<221> NAME/KEY: THIOETH
<222> LOCATION: (8)..(11)
<223> OTHER INFORMATION:
<221> NAME/KEY: THIOETH
<222> LOCATION: (16)..(21)
<223> OTHER INFORMATION:
<221> NAME/KEY: THIOETH
<222> LOCATION: (19)..(22)
<223> OTHER INFORMATION:

<400> SEQUENCE: 9

Phe Lys Xaa Trp Xaa Phe Xaa Xaa Pro Gly Xaa Ala Arg Xaa Gly Xaa
1               5                   10                  15

Phe Asn Xaa Tyr Xaa Xaa
            20

<210> SEQ ID NO 10
<211> LENGTH: 22
<212> TYPE: PRT
<213> ORGANISM: Streptococcus mutans
<220> FEATURE:
<221> NAME/KEY: MISC_FEATURE
<222> LOCATION: (3)..(3)
<223> OTHER INFORMATION: alanyl moiety of lanthionine
<221> NAME/KEY: MISC_FEATURE
<222> LOCATION: (7)..(7)
<223> OTHER INFORMATION: alanyl moiety of lanthionine
<221> NAME/KEY: MISC_FEATURE
<222> LOCATION: (11)..(11)
<223> OTHER INFORMATION: alanyl moiety of lanthionine
<221> NAME/KEY: MISC_FEATURE
<222> LOCATION: (16)..(16)
<223> OTHER INFORMATION: alanyl moiety of lanthionine
<221> NAME/KEY: MISC_FEATURE
<222> LOCATION: (21)..(21)
<223> OTHER INFORMATION: alanyl moiety of lanthionine
<221> NAME/KEY: MISC_FEATURE
<222> LOCATION: (5)..(5)
<223> OTHER INFORMATION: 2,3-didehydroalanine
<221> NAME/KEY: MISC_FEATURE
<222> LOCATION: (19)..(19)
<223> OTHER INFORMATION: 2,3-didehydroalanine
```

```
<221> NAME/KEY: MISC_FEATURE
<222> LOCATION: (8)..(8)
<223> OTHER INFORMATION: S-2-aminobutyric acid
<221> NAME/KEY: MISC_FEATURE
<222> LOCATION: (14)..(14)
<223> OTHER INFORMATION: 2,3-didehydrobutyrine
<221> NAME/KEY: MISC_FEATURE
<222> LOCATION: (22)..(22)
<223> OTHER INFORMATION: S-[aminovinyl]-cysteine
<221> NAME/KEY: THIOETH
<222> LOCATION: (3)..(7)
<223> OTHER INFORMATION:
<221> NAME/KEY: THIOETH
<222> LOCATION: (8)..(11)
<223> OTHER INFORMATION:
<221> NAME/KEY: THIOETH
<222> LOCATION: (16)..(21)
<223> OTHER INFORMATION:
<221> NAME/KEY: THIOETH
<222> LOCATION: (19)..(22)
<223> OTHER INFORMATION:

<400> SEQUENCE: 10

Phe Lys Xaa Trp Xaa Phe Xaa Xaa Pro Gly Xaa Ala Lys Xaa Gly Xaa
1               5                   10                  15

Phe Asn Xaa Tyr Xaa Xaa
            20

<210> SEQ ID NO 11
<211> LENGTH: 22
<212> TYPE: PRT
<213> ORGANISM: Streptococcus mutans
<220> FEATURE:
<221> NAME/KEY: MISC_FEATURE
<222> LOCATION: (3)..(3)
<223> OTHER INFORMATION: alanyl moiety of lanthionine
<221> NAME/KEY: MISC_FEATURE
<222> LOCATION: (7)..(7)
<223> OTHER INFORMATION: alanyl moiety of lanthionine
<221> NAME/KEY: MISC_FEATURE
<222> LOCATION: (11)..(11)
<223> OTHER INFORMATION: alanyl moiety of lanthionine
<221> NAME/KEY: MISC_FEATURE
<222> LOCATION: (16)..(16)
<223> OTHER INFORMATION: alanyl moiety of lanthionine
<221> NAME/KEY: MISC_FEATURE
<222> LOCATION: (21)..(21)
<223> OTHER INFORMATION: alanyl moiety of lanthionine
<221> NAME/KEY: MISC_FEATURE
<222> LOCATION: (5)..(5)
<223> OTHER INFORMATION: 2,3-didehydroalanine
<221> NAME/KEY: MISC_FEATURE
<222> LOCATION: (8)..(8)
<223> OTHER INFORMATION: S-2-aminobutyric acid
<221> NAME/KEY: MISC_FEATURE
<222> LOCATION: (14)..(14)
<223> OTHER INFORMATION: 2,3-didehydrobutyrine
<221> NAME/KEY: MISC_FEATURE
<222> LOCATION: (22)..(22)
<223> OTHER INFORMATION: S-[aminovinyl]-cysteine
<221> NAME/KEY: THIOETH
<222> LOCATION: (3)..(7)
<223> OTHER INFORMATION:
<221> NAME/KEY: THIOETH
<222> LOCATION: (8)..(11)
<223> OTHER INFORMATION:
<221> NAME/KEY: THIOETH
<222> LOCATION: (16)..(21)
<223> OTHER INFORMATION:
<221> NAME/KEY: THIOETH
<222> LOCATION: (19)..(22)
<223> OTHER INFORMATION:
<221> NAME/KEY: MISC_FEATURE
<222> LOCATION: (19)..(19)
<223> OTHER INFORMATION: alanyl moiety of lanthionine
```

-continued

```
<400> SEQUENCE: 11

Phe Lys Xaa Trp Xaa Phe Xaa Xaa Pro Gly Xaa Ala Lys Xaa Gly Xaa
1               5                   10                  15

Phe Asn Xaa Tyr Xaa Xaa
            20

<210> SEQ ID NO 12
<211> LENGTH: 22
<212> TYPE: PRT
<213> ORGANISM: Streptococcus mutans

<400> SEQUENCE: 12

Phe Lys Ser Trp Ser Leu Cys Thr Pro Gly Cys Ala Arg Thr Gly Ser
1               5                   10                  15

Phe Asn Ser Tyr Cys Cys
            20
```